United States Patent [19]
Johnson et al.

[11] Patent Number: 5,604,585
[45] Date of Patent: Feb. 18, 1997

[54] PARTICLE DETECTION SYSTEM EMPLOYING A SUBSYSTEM FOR COLLECTING SCATTERED LIGHT FROM THE PARTICLES

[75] Inventors: Ralph Johnson, Los Gatos; Keith Wells, Santa Cruz; Lee K. Galbraith, San Diego, all of Calif.

[73] Assignee: Tencor Instruments, Santa Clara, Calif.

[21] Appl. No.: 412,331

[22] Filed: Mar. 31, 1995

[51] Int. Cl.⁶ .................................................. G01N 21/88
[52] U.S. Cl. ............................................................ 356/237
[58] Field of Search ................................... 356/237, 338, 356/340, 418, 419, 331; 250/227.28, 227.29

[56] References Cited

U.S. PATENT DOCUMENTS

| | | | |
|---|---|---|---|
| 3,409,374 | 11/1968 | McPherson | 356/331 |
| 3,549,264 | 12/1970 | Christie | 250/227.29 |
| 3,986,778 | 10/1976 | Mathisen et al. | 250/227.29 |
| 4,084,909 | 4/1978 | Mathisen et al. | 356/418 |
| 4,402,607 | 9/1983 | McVay et al. | 356/338 |
| 4,441,124 | 4/1984 | Heebner et al. . | |
| 4,541,715 | 9/1985 | Akiyama et al. | 356/237 |
| 4,601,576 | 7/1986 | Galbraith . | |
| 4,707,134 | 11/1987 | McLachlan et al. | 250/227.29 |
| 4,804,271 | 2/1989 | Cammann | 356/419 |
| 4,898,471 | 2/1990 | Stonestrom et al. . | |
| 5,146,082 | 9/1992 | Abe | 250/227.29 |
| 5,214,494 | 5/1993 | Inaba et al. | 356/419 |
| 5,288,992 | 2/1994 | Fohl | 250/227.28 |
| 5,317,380 | 5/1994 | Allemand . | |

*Primary Examiner*—Richard A. Rosenberger
*Attorney, Agent, or Firm*—Majestic, Parsons, Siebert & Hsue

[57] ABSTRACT

Light scattered from illuminated spot on a patterned wafer is first passed through a di-electric filter and then by an optical fiber bundle to a detector. The di-electric filter controls the aperture of the light that is passed to a desired azimuth angle and the optical fiber further limits the aperture.

34 Claims, 10 Drawing Sheets

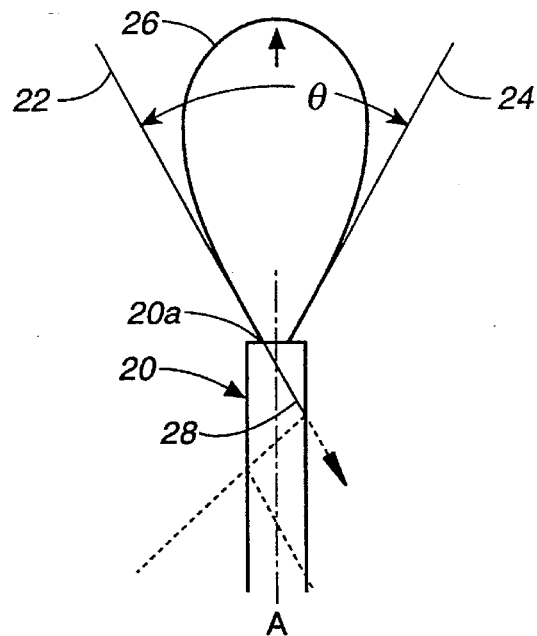
FIG._1
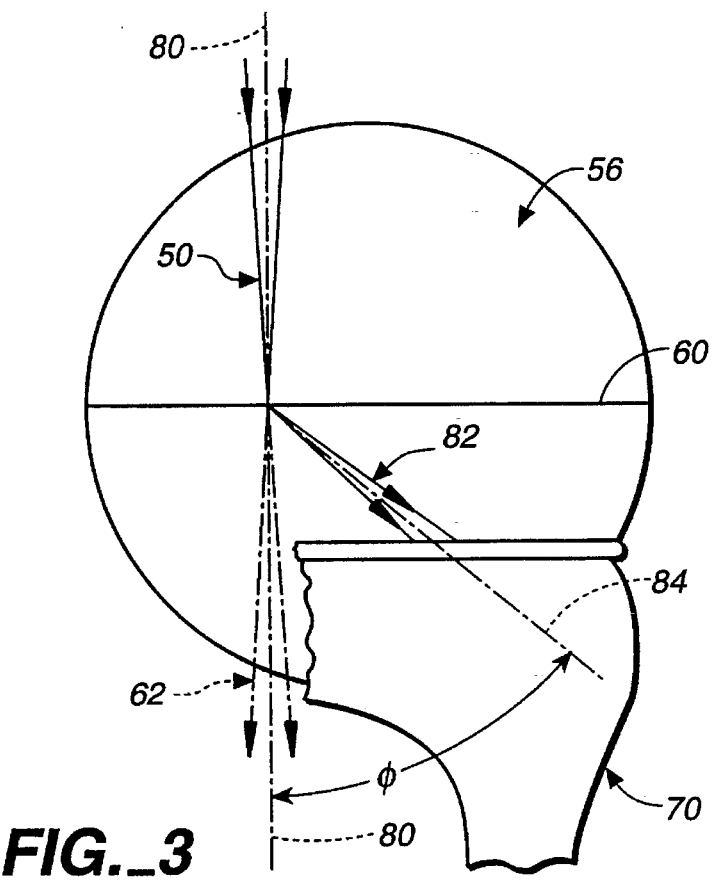
FIG._3

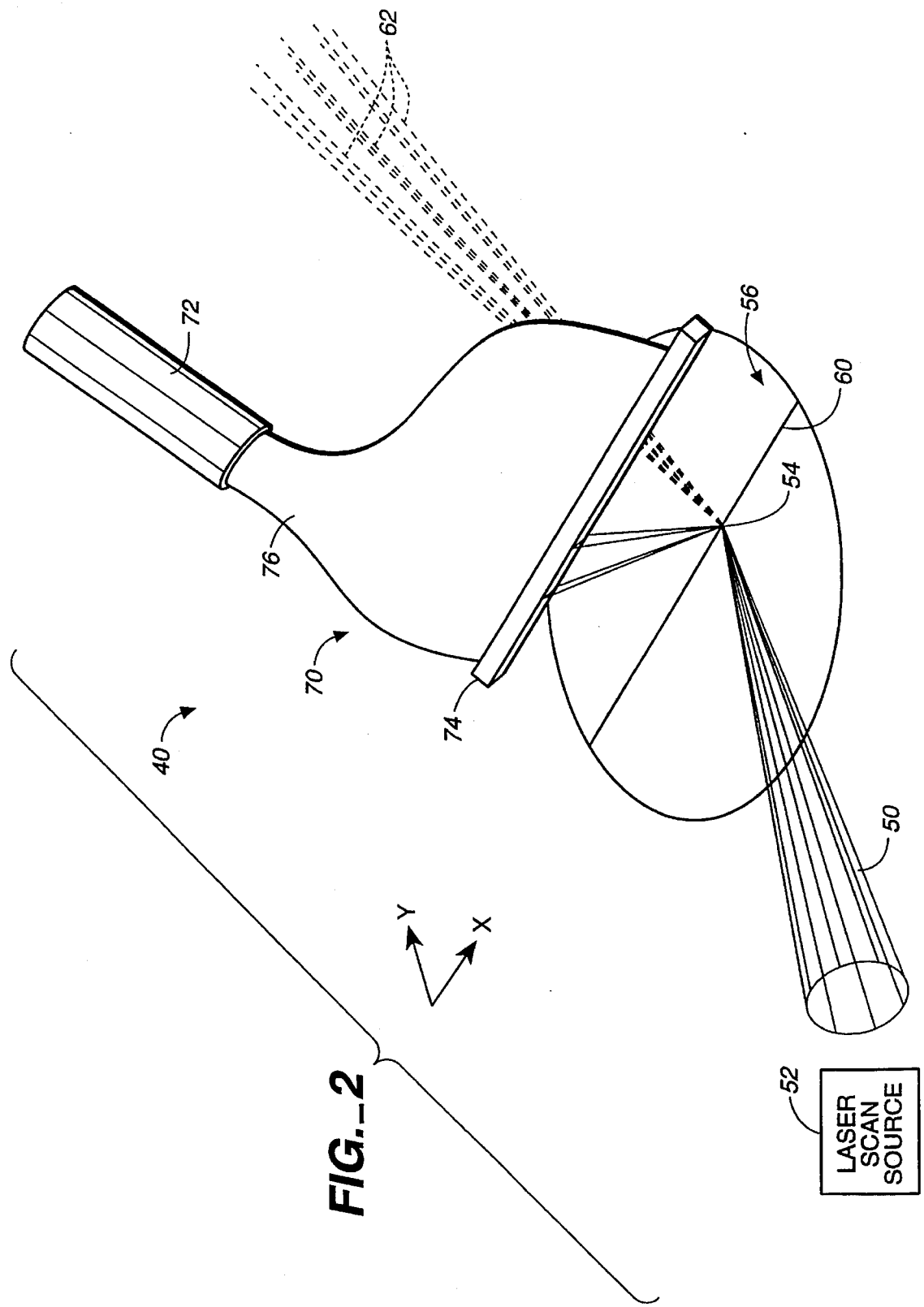
FIG._2

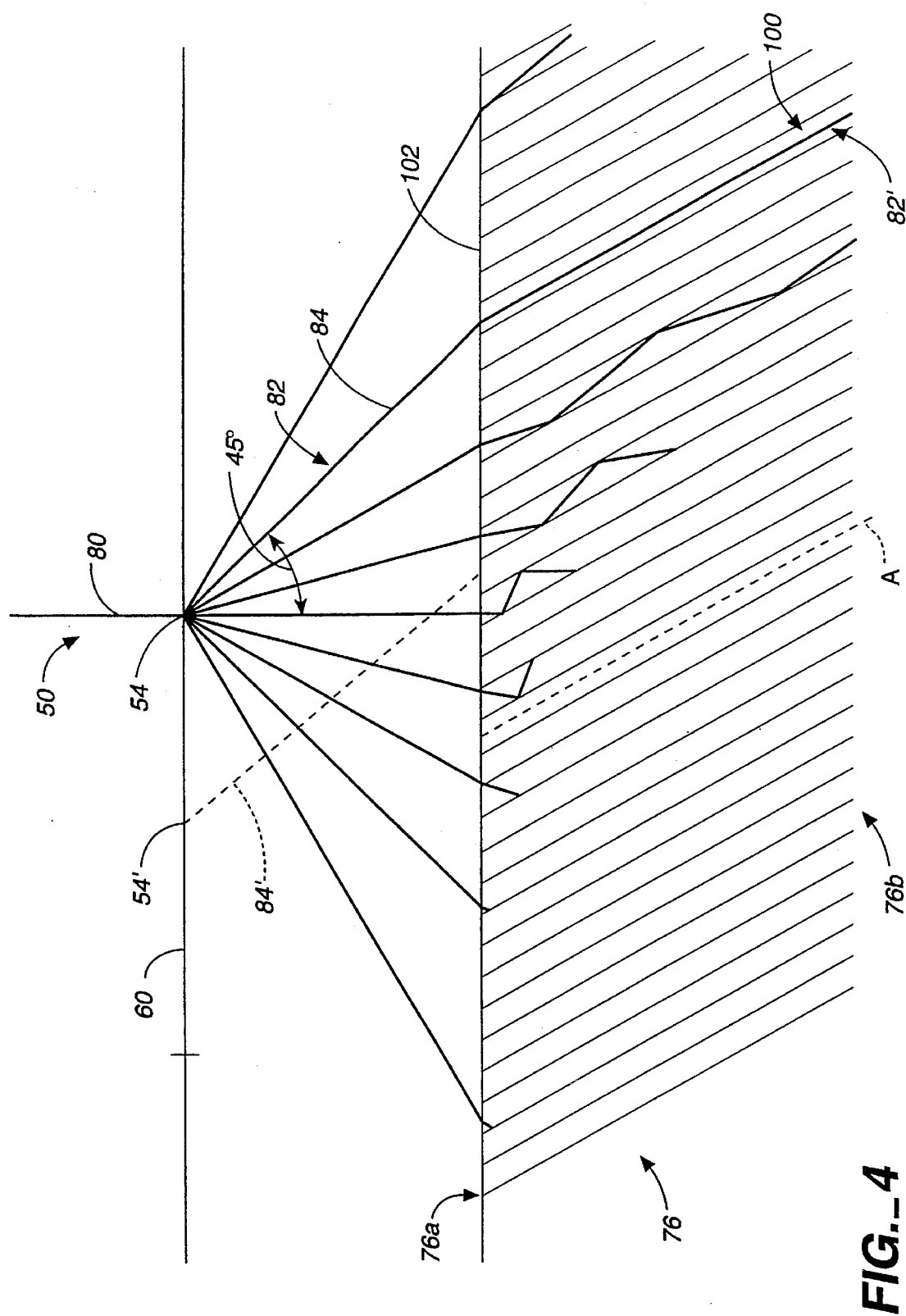
FIG._4

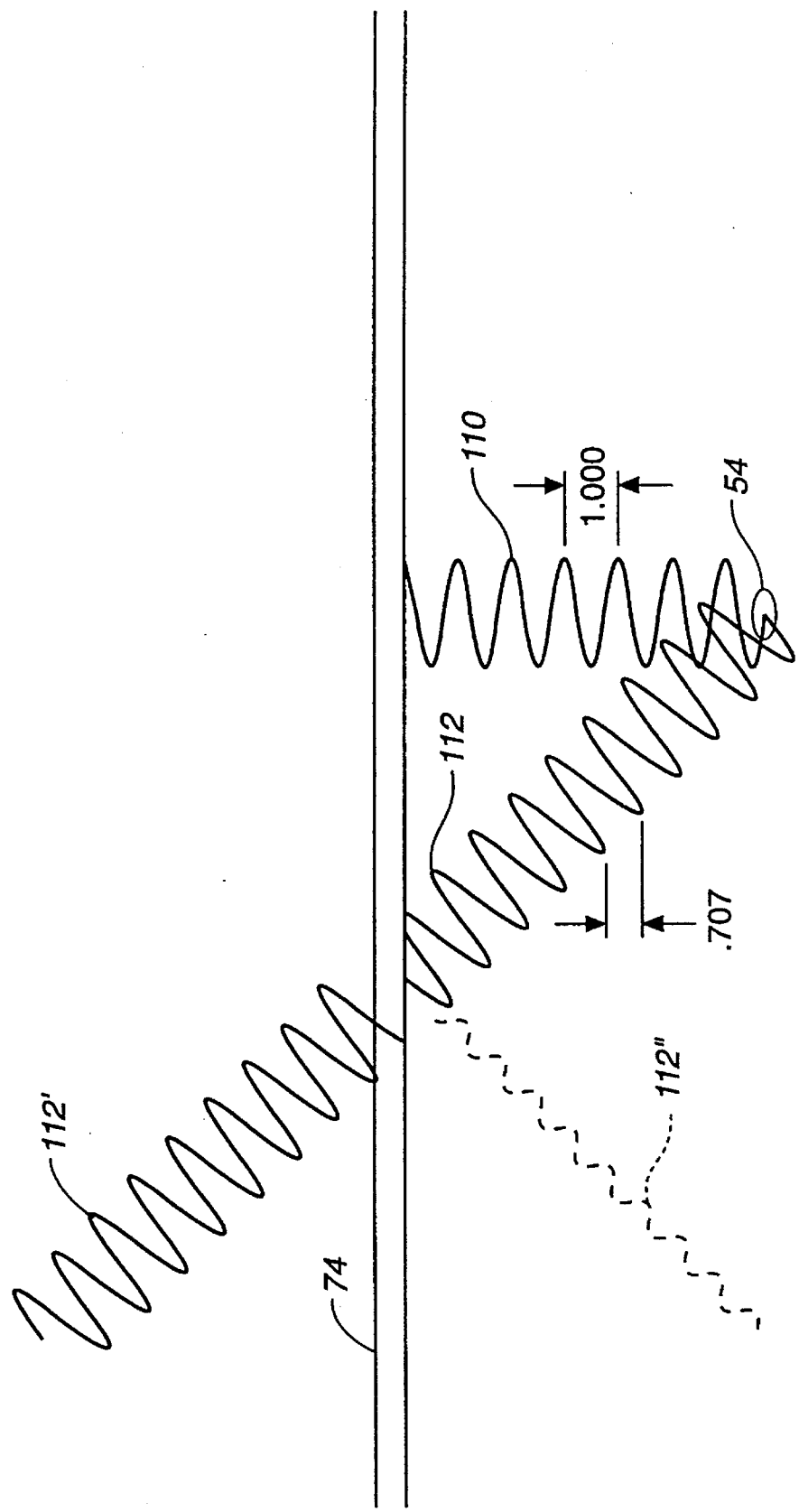
FIG._5

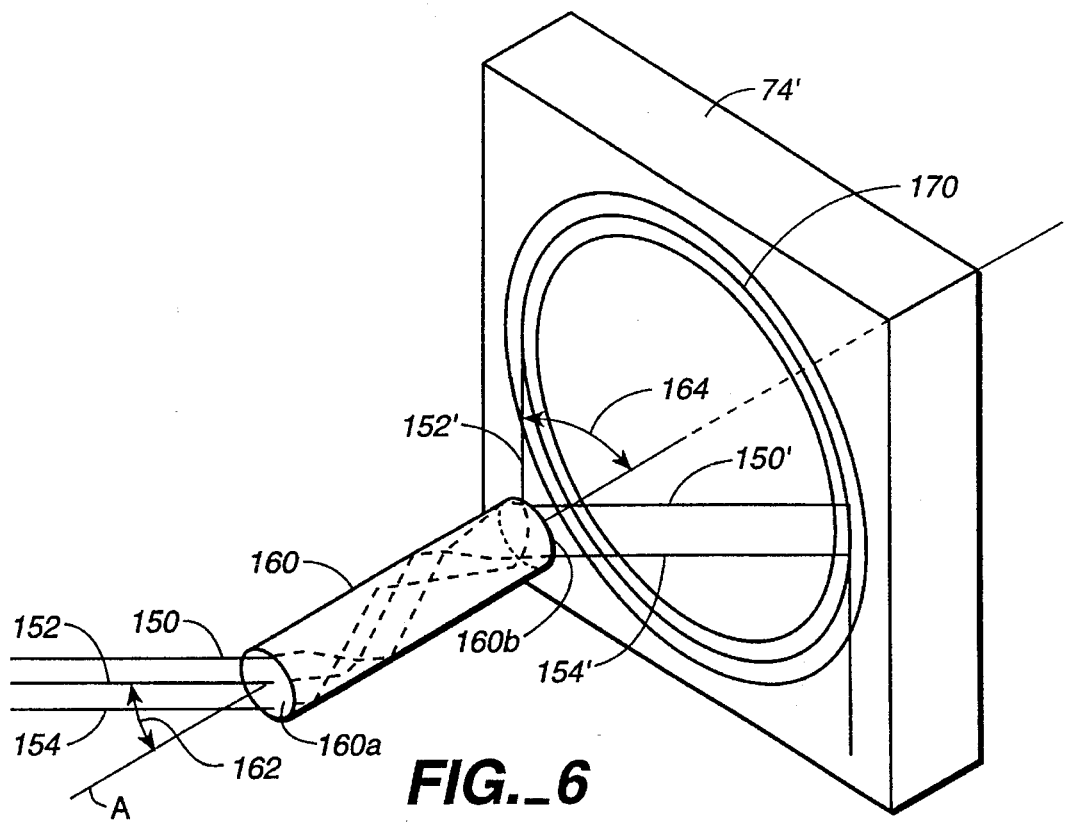
FIG._6
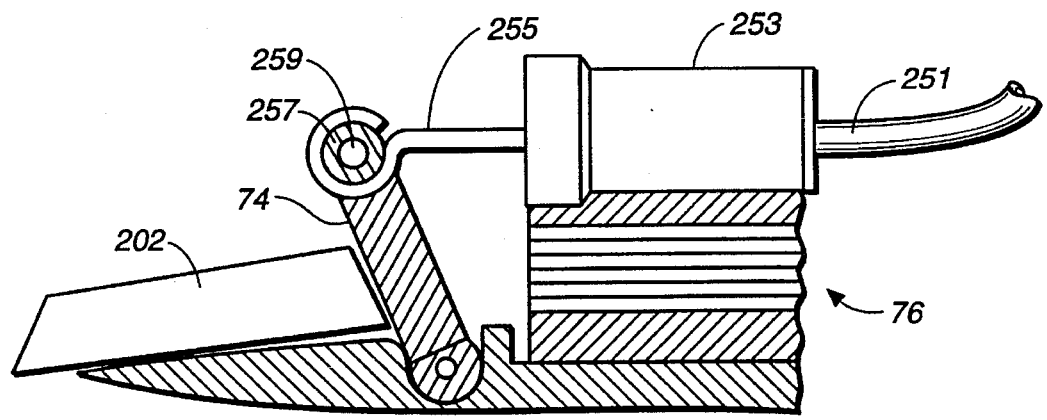
FIG._10

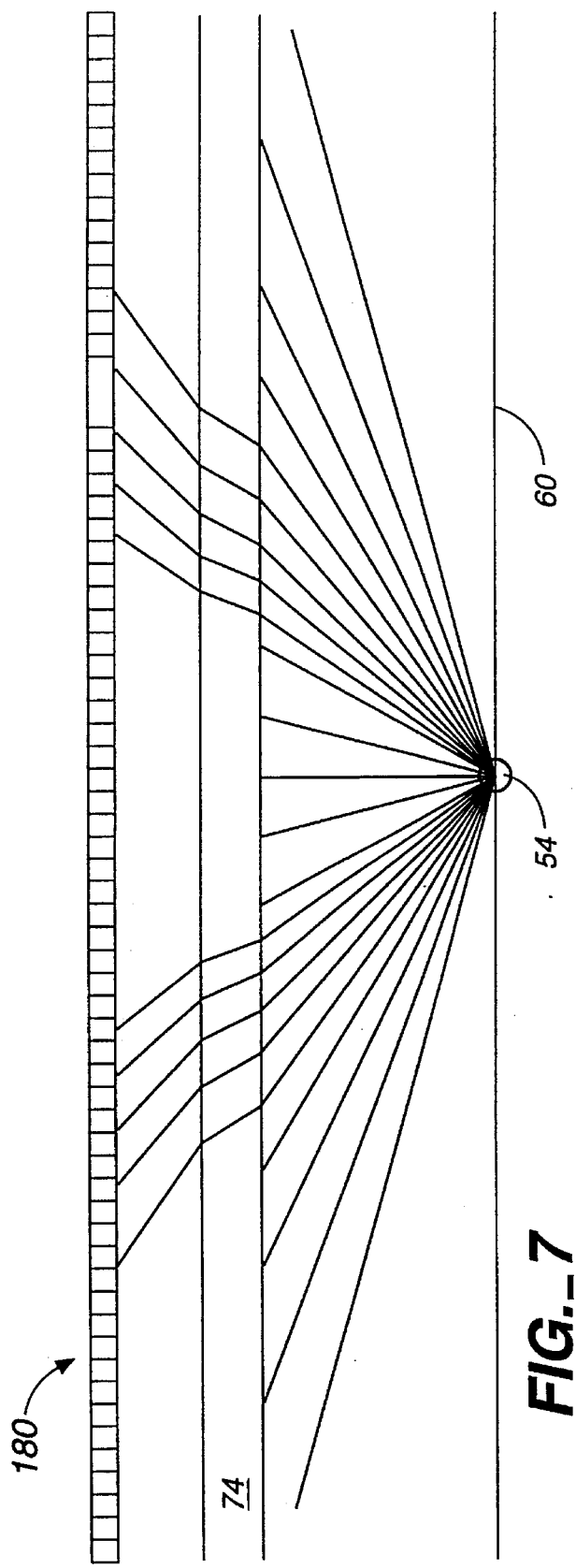
FIG._7

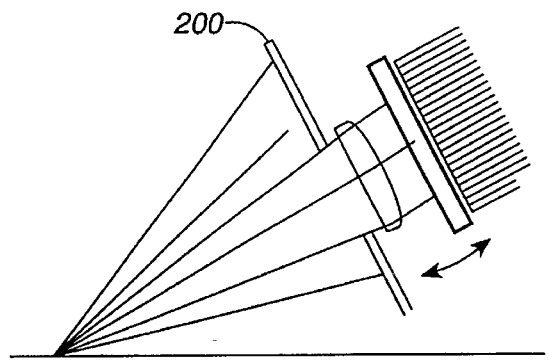
FIG._8A
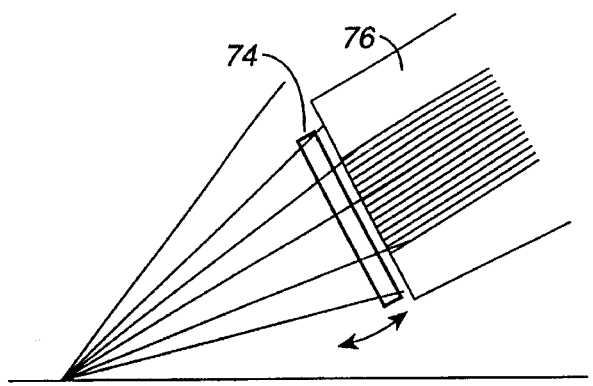
FIG._8B
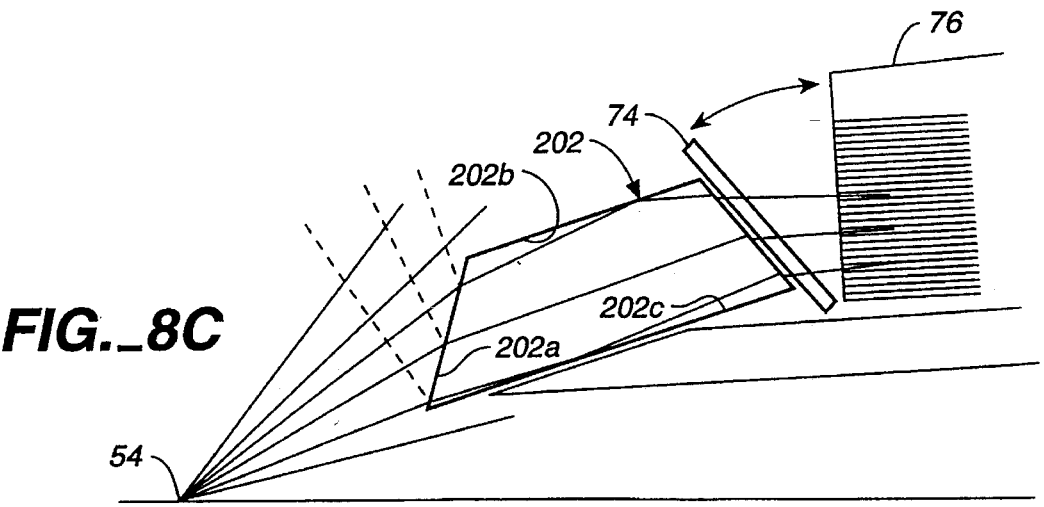
FIG._8C

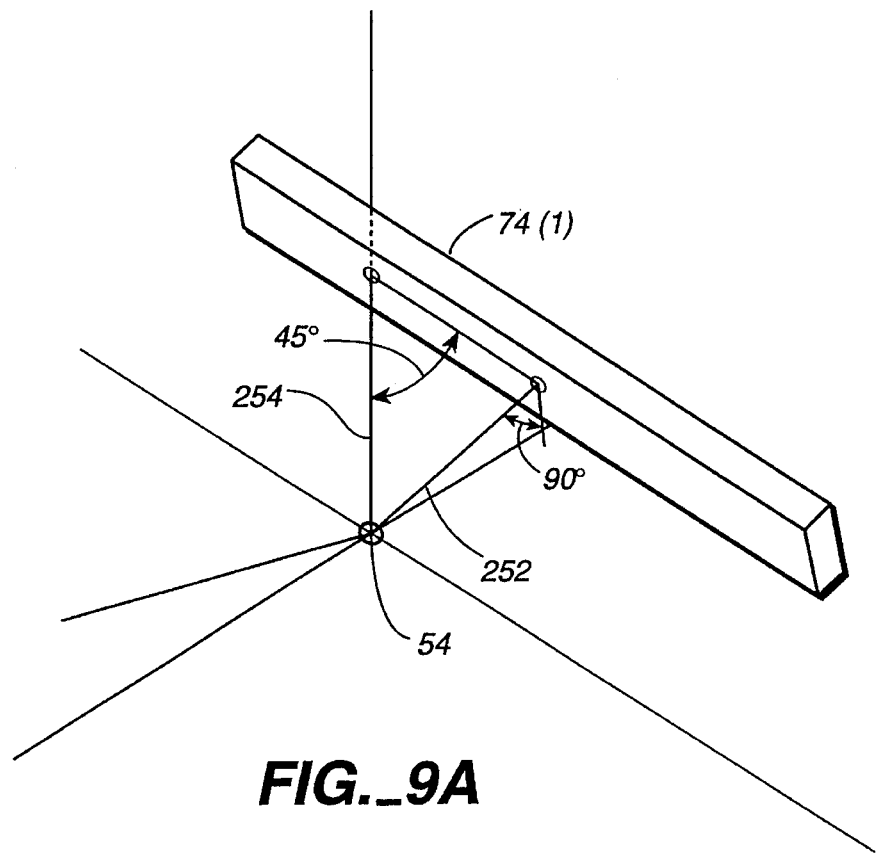
FIG._9A
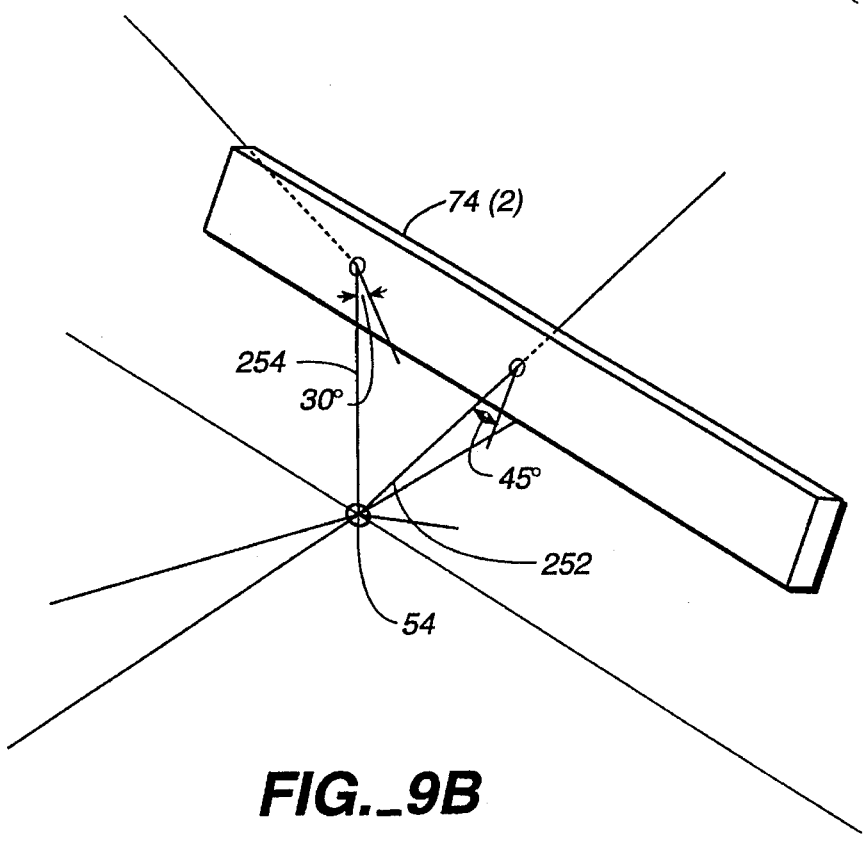
FIG._9B

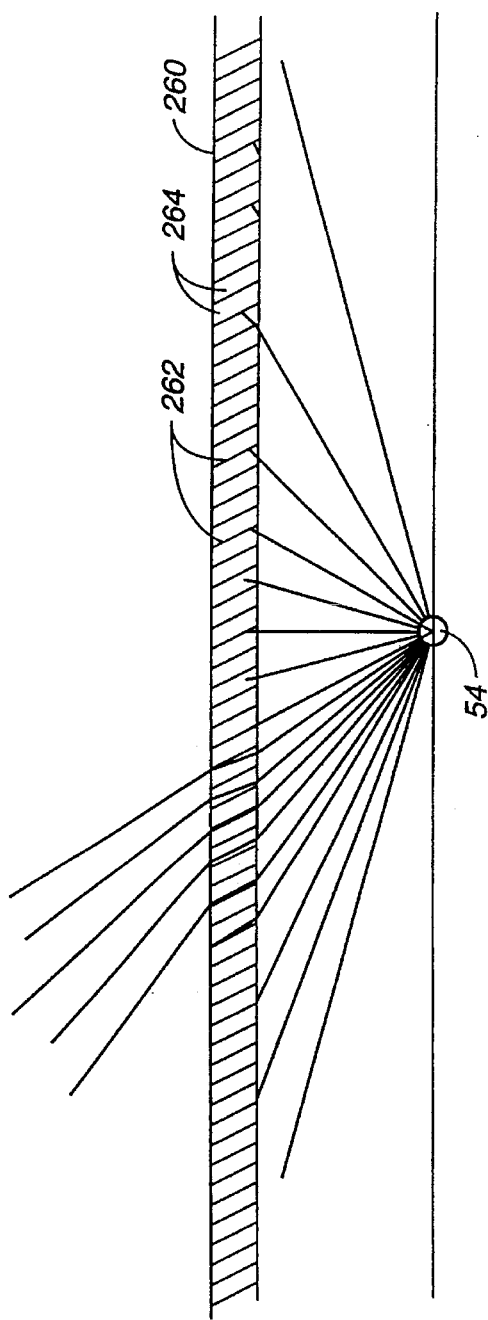
FIG._11
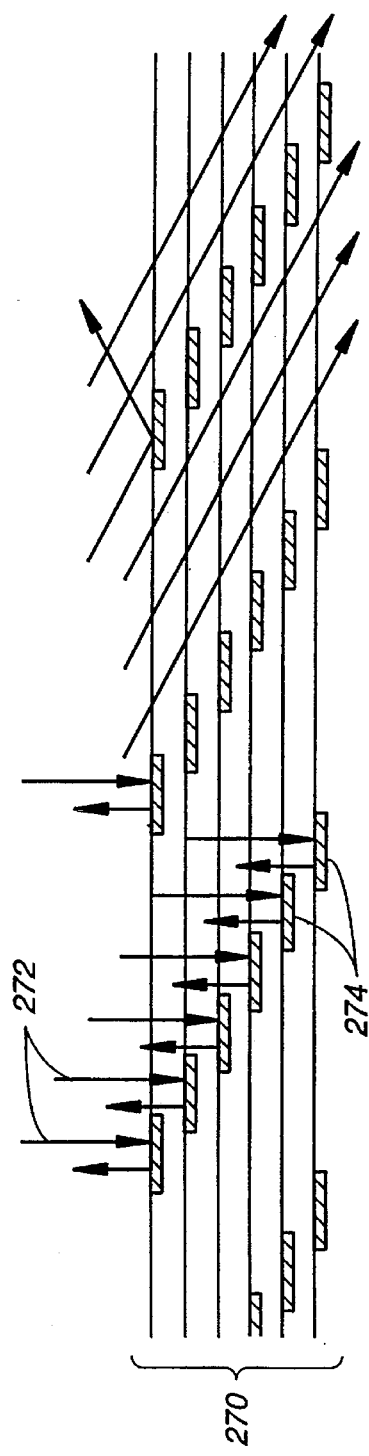
FIG._12

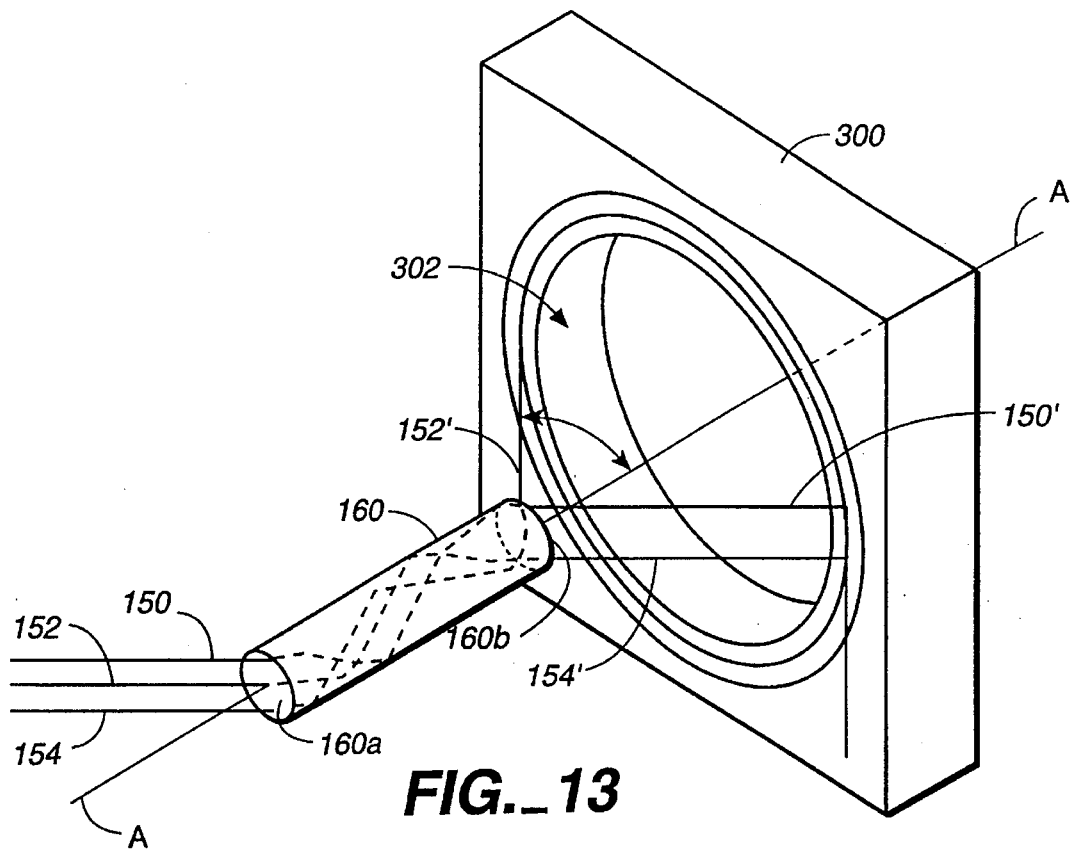
FIG._13
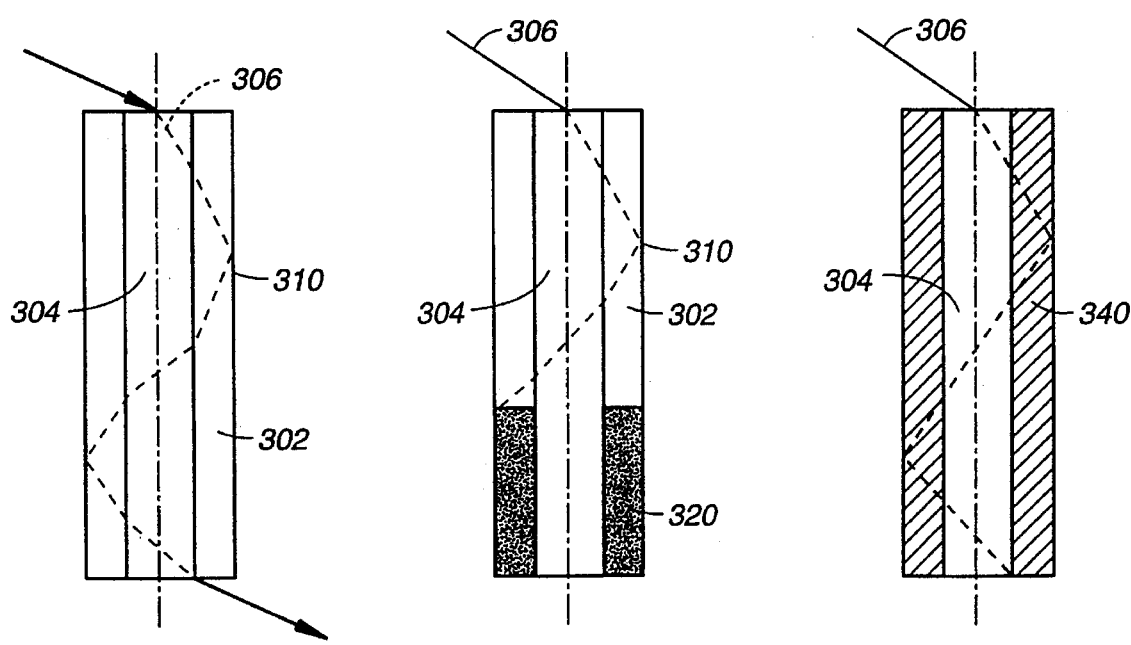
FIG._14A        FIG._14B        FIG._14C

1

PARTICLE DETECTION SYSTEM EMPLOYING A SUBSYSTEM FOR COLLECTING SCATTERED LIGHT FROM THE PARTICLES

BACKGROUND OF THE INVENTION

This invention relates in general to systems for particle detection on surfaces and, in particular, to a particle detection system employing a subsystem for collecting light from surfaces within predetermined apertures or collection angles.

In the process of manufacturing devices such as semiconductor wafers, flat panel displays, photomasks, ceramic substrates and other devices, it is important to detect contaminant particles on the surface of an object using the principle of light scattering. In U.S. Pat. No. 4,898,471 assigned to Tencor Instruments, the assignee of the present application, a system for detecting particles and other defects on a patterned semiconductor wafer, photomask or the like is disclosed. A polarizing filter is used in the system to polarize the beam of light in the direction substantially parallel to the surface of the patterned semiconductor wafer to be examined. The beam is enlarged in cross-sectional diameter by a beam expander placed along the path of the beam after the polarizing filter. The beam is then caused to scan by a deflection mirror. The scanning beam is then focused on the patterned wafer at a grazing angle of incidence along an incident direction that is substantially parallel to the patterned streets formed on the wafer. A light collection system for detecting scattered light is positioned in an azimuth direction in a range from about 80°–100° from the incident direction of the scanning beam. The light collection system includes a lens for focusing the scattered light, a polarizing filter oriented in a direction substantially parallel to the surface of the patterned wafer and a photomultiplier tube.

In many semiconductor wafers, such as those formed in manufacturing logic devices, 45° geometries are prevalent, either as interconnects or as repeated feature edges. If the 45° geometries are small in size relative to the wavelength of the incident scanning beam and spot size, the diffraction generated by such geometries can be filtered in the Fourier plane with a programmed blockage. If such geometries are irregularly shaped or are widely spaced apart, it may be difficult to filter the diffraction pattern at the Fourier plane.

Given a known diffraction pattern from the geometries of the pattern on the semiconductor wafer, it may be possible to design a light collection system that would avoid the high intensity pattern scatter in specific directions. However, since the path of the scanning beam covers the entire length or width of the wafer, the scattered light can originate from any point of the long scan line. If the scanning beam has a cross-section that is large relative to the size of the particles being detected, specular reflection and some components of reflection from patterned features would contain many times the light radiated from the particles. Thus the light collection system would have to be designed to avoid the specular reflection and reflection from patterned features originating from any point on the long scan line.

To detect defects on the patterned wafer, one existing technique is to construct templates from the scattered light from individual die of the wafer and comparing the template to the scattered light from other die on the wafer. Both pattern features and contamination have specific and often extremely selective radiation patterns. In order for the comparison to the template to be meaningful, it is very desirable for the light collection system to collect light at a constant collection angle; existing particle detection systems for patterned wafers have used Fourier plane stops to limit the aperture of the system. While this can be achieved for any collection angle, due to the long scan length discussed above, and the need to avoid specular beams from geometries such as the 45° geometries on the wafers, it may be difficult to design a light collection system that is practical. In many instances, the optical system simply becomes too large for users.

From the above, none of the particle detection systems and the light collection subsystems they employ are entirely satisfactory. It is therefore desirable to provide an improved particle detection system and an improved light collection subsystem in which the above-described difficulties are alleviated.

SUMMARY OF THE INVENTION

One aspect of the invention is based on the observation that, by using one or more optical fibers to collect the scattered light and orienting the optical fibers at predetermined directions relative to the incident direction of the scanning beam to receive the scattered light at an azimuth angle different from 90°, many of the difficulties described above can be avoided. The one or more optical fibers inherently have capture or collection angles in which they collect light, so that light originating outside of such capture or collection angles will be severely attenuated and fail to emerge in significant intensity when passed through the fibers. Therefore, by orienting the optical fibers at predetermined directions relative to the incident direction of the scanning beam, it is possible to reduce the amount of high intensity reflections and scatter reaching the fibers while collecting signal from the desired features. In particular, to avoid the reflections caused by 45° geometries on the patterned wafer, the optical fibers are oriented at such directions that they will receive light scattered at azimuth angles different from 90°.

Thus one aspect of the invention is directed towards an apparatus for detecting particles on a surface, comprising a source supplying light along an incident direction to a region on the surface and one or more optical fibers oriented in predetermined directions relative to the incident direction to receive light scattered from said region at an azimuth angle different from 90°. A related aspect of the invention is directed towards a method for detecting particles on a patterned surface of a semiconductor material. The method comprises supplying light along an incident direction to a region on the surface, and orienting one or more optical fibers at predetermined angles to the incident direction to receive light scattered from said region at an azimuth angle different from 90°.

A bandpass filter composed of a di-electric stack can be designed to transmit light of a specific wavelength at a specific range of angles relative to the direction normal to the surface of the di-electric stack, while reflecting light of the same wavelength that impinges the stack surface at angles outside the range. This range of passed light creates an angular collection aperture, and is referred to in this application as the aperture or collection aperture. This filter may be used to control the aperture of a light collection system in order to reduce the amount of undesirable light collected by the light collection system. Thus another aspect of the invention is directed towards an apparatus for collecting light. The apparatus comprises a filter including a di-electric material that passes light of a predetermined wavelength substantially only within said aperture, and an optical system collecting light that passed through the filter.

Depending on which portion of the end face of an optical fiber that a specular beam strikes, the specular beam may still emerge from the fiber at the other end even if the specular beam is outside the capture or collection angle of the fiber. Thus detection accuracy of the system can be improved by employing means for controlling the aperture or collection aperture of the scattered light either before or after the light passes through the fiber. Thus another aspect of the invention is directed towards an apparatus for detecting particles on the surface, comprising a source supplying light to a region on the surface, and one or more optical fibers oriented to receive light scattered from said region. The apparatus further comprises means for controlling the aperture of the scattered light before or after such light passes through the one or more fibers.

Another aspect of the invention is directed towards the light collection subsystem of the particle detection apparatus described immediately above. Yet another aspect of the invention is therefore directed towards an apparatus for collecting light comprising one or more optical fibers oriented to receive light within a capture or collection angle and means for controlling the aperture of the scattered light before or after such light passes through the one or more fibers.

An aspect of the invention related to that above is directed towards a method for detecting particles on the surface of a semiconductor material, comprising supplying light to a region on the surface, orienting one or more optical fibers to receive light scattered from said region and controlling the aperture of the scattered light before or after such light passes through the one or more fibers. Yet another related aspect of the invention is directed towards a method for collecting light, comprising orienting one or more optical fibers to receive light within an aperture or collection angle, and controlling the aperture of the scattered light before or after such light passes through the one or more fibers.

With the elevation angle of light collection constrained by the optical fiber geometry or other apertures, it is desirable to be able to alter the azimuth angle of light collection by tilting the di-electric filter to change the incident angle of the light beam relative to the light collecting surface of the filter. If the tilting causes the light collecting surface of the filter to have a different orientation in the elevation plane, the light beam will impinge the light collecting surface at a different incident angle, thereby altering the collection aperture of the system.

Thus one more aspect of the invention is directed towards an apparatus for collecting light, comprising a filter including a di-electric material that passes light of a predetermined wavelength substantially only when said light is within a predetermined collection aperture, and means for moving the filter to alter the orientation of the material, thereby altering the collection aperture. Another related aspect of the invention is directed towards a method for collecting light, comprising providing a filter including a di-electric material that passes light of a predetermined wavelength substantially only when said light is within a predetermined collection aperture, and moving the material to alter its orientation, thereby altering the collection aperture.

The above-described feature where the di-electric material is moved to alter the collection aperture may be used in a system for detecting particles. Therefore, another aspect of the invention is directed towards an apparatus for detecting particles on the surface, comprising a source supplying a scanning beam of light to the surface, causing scattered light to travel along different directions, a filter including a di-electric material that passes light of a predetermined wavelength substantially only when said light is within a collection aperture, and means for moving the material to alter its orientation, thereby altering the collection aperture. Yet another aspect of the invention is directed towards a method for detecting particles on the surface, comprising supplying a scanning beam of light to the surface, causing scattered light that travels along different directions, providing a filter including a di-electric material that passes the scattered light of a predetermined wavelength substantially only when said scattered light is within a predetermined collection aperture, and moving the material to alter its orientation, thereby altering the collection aperture.

BRIEF DESCRIPTION OF THE DRAWINGS

FIG. 1 is a schematic view of an end portion of an optical fiber illustrating its collection aperture or capture angle to illustrate the invention.

FIG. 2 is a perspective view of a particle detection system to illustrate the preferred embodiment of the invention.

FIG. 3 is a top view of a portion of the system of FIG. 2.

FIG. 4 is a schematic view of a collection of optical fibers in a bundle and the paths of scattered light towards the bundle to illustrate the invention.

FIG. 5 is a schematic view of a filter made of a di-electric material and the paths of light beams to illustrate another aspect of the invention.

FIG. 6 is a schematic view of a section of an optical fiber and the paths of light emerging from the fiber and a filter for filtering the light emerging from the fiber to illustrate another aspect of the invention.

FIG. 7 is a schematic view of the filter of FIG. 5 and a light collection system to illustrate the invention.

FIGS. 8A–8C are schematic views of control systems for controlling the elevation collection angle to illustrate the invention.

FIGS. 9A, 9B are schematic views illustrating how the di-electric filter of FIG. 5 can be rotated to control the collection angle or aperture for illustrating another aspect of the invention.

FIG. 10 is a side view showing in more detail the control mechanism of FIG. 8C to illustrate the aspect of FIGS. 9A, 9B.

FIGS. 11 and 12 are schematic views of respectively a baffle and a grading type aperture control device that can be used instead of a di-electric filter to illustrate yet other aspects of the invention.

FIG. 13 is an isometric view parallel to that of FIG. 6 illustrating an aperture control device that can be used to replace the di-electric filter of FIG. 6.

FIGS. 14A, 14B, 14C are cross-sectional views of a section of an optical fiber, each with a different cladding composition or material to illustrate another aspect of the invention.

For simplicity in description, identical components are labeled by the same numerals in this application.

DETAILED DESCRIPTION OF THE PREFERRED EMBODIMENT

FIG. 1 is a schematic view of an end portion of an optical fiber to illustrate its capture or collection angle. Fiber 20 has a capture or collection angle theta. As shown in FIG. 1, the capture angle theta is bounded by the two extreme positions 22, 24 of light rays that would impinge upon a center portion of the end face 20a of fiber 20, pass through the fiber to emerge at the other end of the fiber with significant intensity. Balloon 26 is a graphical plot representing the amount of light transmitted at a corresponding angle to the axis A of the fiber. Thus the light transmission at points directly on the axis A would be 100%, with transmission loss gradually increasing with the angle away from axis A until the extreme positions 22, 24 are reached, beyond which insignificantly amount of light will be transmitted by the fiber. FIG. 1 illustrates the passage of light rays that impinge upon end face 20a outside of the collection or capture angle. As illustrated in FIG. 1, each internal reflection within fiber 20 of light rays 28 slightly beyond the extreme positions 22, 24 would cause a loss of light intensity. For this reason, light rays that impinge end face 20a at an oblique angle are likely to be totally lost and unlikely to pass through fiber 20 to emerge at the other end.

In the description below, the features of the invention are illustrated by reference to patterned surfaces, such as surfaces of patterned wafers, although the invention is just as applicable to bare wafer detection and light collection. FIG. 2 is an isometric view of a particle detection system 40 including a light collection subsystem 70 to illustrate the preferred embodiment of the invention. As shown in FIG. 2, a laser beam 50 is generated by a laser scan source 52 which can cause beam 50 to scan a surface. Laser beam 50 is directed towards a spot or portion 54 of a wafer surface 56. As known to those skilled in the art and discussed in U.S. Pat. No. 4,898,471 referenced above, laser beam 50 is caused to move in a scanning motion so that spot 54 traces a scan line 60 on wafer surface 56, along the X direction, parallel to streets between die.

A stage (not shown) moves the wafer along the Y direction so that spot 54 would in time be directed to cover every portion of the surface 56 of the wafer. The specular reflection of beam 50 from the unpatterned portions of surface 56 is shown along dotted lines 62. Aside from the specular reflection from the unpatterned portions of surface 56, the patterned portions as well as contaminant particles that are illuminated within spot 54 scatter light. A portion of such scattered light is collected by a light collection subsystem 70, and the light so collected is directed towards a detector 72 for analysis of wafer surface 56. Subsystem 70 includes a filter 74 and bundle of optical fibers 76.

Certain particular geometries of devices on surface 56 would cause high intensity specular beams or defraction patterns to be emitted at particular directions relative to the incident direction of beam 50. For example, 45° geometries in spot 54 would cause strong pattern light signals to be directed in a cone having strong intensity components in directions at 90 degrees to the illuminating beam 50, such as directions at 90 degrees azimuth angle. One of the aspects of the invention is based on the observation that optical fibers have collection or capture angles and therefore can be placed at the desired locations to avoid the strong pattern signals and to maximize the chance of detecting anomalies on the wafer surface 56.

FIG. 3 is a top view of a portion of the light collection system 70, the wafer and a schematic representation of beam 50 and reflection 62 of FIG. 2, where a portion of the bundle 76 has been cut away to expose the reflection 62. Beam 50 of course has a certain width and so does its specular reflection 62. Line 80 within beam 50 may be chosen to represent the incident direction (e.g., as an average direction of the beam) of the beam 50. Similarly, the scattered light 82 that is collected by system 70 also has a spread, but its average direction can again be represented by a line 84. The angle phi between the incident direction 80 and direction 84 as seen from the top view is known as the azimuth angle of the scattered light beam 82, and the term "azimuth angle" will be used with such meaning in this application. Beam 82 also has an elevation angle that it makes with surface 56 when viewed from the side. If phi is less than 90 degrees, beam 82 is a forward scattering beam; if phi is greater than 90 degrees, beam 82 is a back scattering beam. The collection scheme of this invention is symmetrical and can be used for both forward as well as back scattering systems.

FIG. 4 is a schematic view of the incident beam 50, scan line 60, the fiberoptic bundle 76 of system 70, but omitting filter 74, showing the passage of scattered light through the optical fibers to illustrate the invention. In the preferred embodiment shown in FIG. 2, the light collection system 70 includes a filter 74 and a fiberoptic bundle 76. In some embodiments, it may be possible to omit the filter so that the scattered light would impinge directly onto the end faces 76a of the fibers in bundle 76, as shown in FIG. 4. For simplicity, the incident beam 50 and the scattered beams are represented in FIG. 4 as single lines, it being understood that these beams of course have certain widths. In general the collection of specular beams is avoided by using a different elevation than where most specular reflection occurs; scattering of course occurs in any direction dependent on the surface. As shown in FIG. 4, light impinging on spot 54 can be scattered in a number of directions towards the bundle 76. Bundle 76 includes a number of optical fibers with axes A.

Preferably and as shown in FIG. 4, the end faces 76a of the fibers are not perpendicular to their axes A to allow better collection of scattered light along desired azimuth angles. Light actually collected is determined by intersecting the fiber end face and then by angularly dependent transmission by the fiber. In FIG. 4, the fibers in bundle 76 are constructed so that the passage of light at an azimuth of 45 degrees through the bundle would be optimal. The azimuth angle of beam 82 is about 45°. The end faces 76a of the fibers 76 are at such angles with axes A, and the fibers have such index of refraction that when beam 82 impinges upon end face 102 of fiber 100, such beam would be refracted into beam 82' that travels along or in a direction parallel to the axis A of fiber 100. End face 102 is the boundary between the fiber 100 and air, which has index of refraction of 1. Thus according to Snell's Law, where the index of refraction of the fiberoptic material is 1.6, end face 102 is approximately at 65° angle to axis A. The reason for finishing the fibers at such angle and as shown is to allow mass polishing and to avoid introduction of scatter between fibers.

As shown in FIG. 4, light from spot 54 is scattered in many directions other than direction 84. Such beams also impinge on the end faces 76a of fibers in bundle 76. Where such scattered light travels in directions far away from direction 84, these beams are typically outside the capture or collection angles of the fibers whose end faces they impinge upon, so that these beams would be severely attenuated through internal reflections and absorption and would therefore fail to emerge in significant intensity from the other end 76b of the bundle.

The aperture control effect inherent in the collection or capture angles of the fibers in bundle 76 may be adequate to discriminate against scattered light away from the desired directions. In FIG. 4, for example, the aperture control effect due to collection angles of the fibers is that only light scattered from spot 54 forming a cone with an axis along direction 84 will be passed by the bundle, while scattered light along other directions will not. When beam 50 is scanned along the scan line 60, spot 54 may move to a new spot 54'. At such location, essentially the same process will be repeated as described above where the scattered light from spot 54' within a cone with axis 84' along a 45° azimuth angle will pass through bundle 76, while scattered light in other directions outside the cone will be rejected and fail to emerge at end 76b of the bundle.

However, as described below, if the incoming light impinges the fiber ends at points near the edges of the fibers, such light will pass through the fibers even though they are outside the collection or capture angles of the fibers. In the preferred embodiment, it is desirable to employ an aperture control device for further aperture control, such as filter 74 in FIG. 2, to only permit light that are on or close to the desired direction 84, 84' to pass and impinge upon end 76 of bundle 76. A filter having such properties is illustrated in FIG. 5 described below.

A di-electric filter 74 may comprise a stack of different layers of di-electric material, where the material will reflect most of the light of a particular wavelength that impinges upon the layer in the normal direction to the layer but would transmit about 80% of the light of the same wavelength if the light impinges upon the layer at a different angle than normal, such as within a range of angles around 45° (defining the aperture or collection aperture of the filter) as illustrated in FIG. 5. In one embodiment, the filter layer 74 is constructed so that it reflects most of the light at wavelength of 488 nanometers (nm) that impinges the layer in a direction normal to the layer but will pass 80% or more of light of such wavelength that impinges the layer at around 45°. Where the light beam impinges the layer at an angle other than 90°, the wavelength as seen by the layer is actually shorter than the actual wavelength of the light. As illustrated in FIG. 5, beam 110 impinging layer 74 at 90° has wavelength W while beam 112 with the same wavelength impinging layer 74 at 45° will have an effective wavelength of 0.707 W instead. Thus 80% of beam 112 will be transmitted by layer 74 as beam 112' and 20% of the incident beam 112 will be reflected as a reflected beam 112". Thus if the laser scan source 52 directs a beam 50 at wavelength 488 nm at spot 54, the reflected light from spot 54 would also be substantially at such wavelength. If such scattered light impinges upon filter 74 in a normal direction, such as beam 110 in FIG. 5, such beam would be reflected, whereas 80% of the light scattered from spot 54 that impinges layer 74 at 45° would be transmitted to bundle 76. An 80% transmission rate in the light collection system 70 has been found to be satisfactory for the purpose of particle detection in system 40 of FIG. 2. It is found that using a filter such as filter 74, only about $10^{-7}$ of the light is transmitted in the normal direction.

The stack of di-electric layers 74 may have a wide range of acceptable angles and rejection performance. Such filters can be made to order according to custom specification (including the apertures or collection apertures of the filters) from many vendors, including for example, CVI Laser Corporation, 200 Dorado Place SE, Albuquerque, N.M. 87192. Bundle 74 may be obtained by binding a large number of optical fibers together and then polishing the bundle at an angle to obtain end face 76a that is at an angle other than 90 degrees to the axes A. Where the end face 76a is not normal to axes A, better light transmission is realized in the collection of scattered light. It is understood that this (end face not normal to axis) is not required, and all the advantages of the invention are obtained as long as the fibers are oriented along directions so that they are adapted to receive scattered light at azimuth angles of other than 90 degrees. Thus, the end faces of the fibers can still be normal to their axes, where the scattered at the desired azimuth angles impinge the end faces at angles equal to or other than 90 degrees. Such and other variations are within the scope of the invention.

As a practical matter, it may be difficult to perfectly align a large number of fibers together in the process of making the bundle 76, so that the fibers in the resulting bundle will not be exactly parallel. For this reason some of the fibers may be oriented in such directions that they will transmit light from azimuths other than those intended by the design. This can result in non-uniform response that is dependent on the location of the feature along the scan line. This can make discrimination of features and machine consistency more difficult. This problem is alleviated by controlling the aperture of the scattered light using filter 74 before the light impinges onto face 76a. Especially where the filter 74 has a collection aperture smaller than the collection or capture angle of the fibers, the fact that some of the fibers are slightly misaligned will not cause collection angle variations.

Instead of placing filter 74 between the scattered light and bundle 76 as described above, it is also possible to instead place the filter between bundle 76 and detector 72 in FIG. 2. This is explained further in reference to FIG. 6.

Applicants have observed that where an incoming light ray impinges upon the end face of an optical fiber where the ray is at a certain incident angle to the axis of the fiber, then the same ray will emerge from the other end of the fiber at an angle to the axis of the fiber substantially equal to the incident angle, although the original orientation of the incoming ray around the fiber axis is not preserved. This is illustrated in FIG. 6. Thus if three incoming rays 150, 152, 154 having the same orientation impinge end 160a of fiber 160 at the same incident angle 162 to axis A, then the three rays will emerge from the other end 160b of the fiber as rays 150', 152', 154' where all three rays 152'–154' will be at angle 164 to axis A substantially equal to incident angle 162, but where the orientation of the exiting rays may frequently differ from the original orientation of the beams as shown in FIG. 6. Thus even though the incoming rays 150–154 all have the same orientation and bear the same angle 162 to axis A, the exiting ray 152' has a different orientation compared to the exiting rays 150', 154'.

Thus if a large number of rays parallel to rays 150–154 impinge the end face 160a of fiber 160, the exiting rays (such as 150', 152', 154') will be spread out to form a sheet that encloses a cone. This sheet of light would impinge upon a surface such as that of filter 74' and appear as an illuminated ring 170. Light rays approaching fiber 160 at angles different from 162, however, will emerge at end face 160b at angles different from 164 to axis A, so that the exiting rays will impinge filter 74' at points outside ring 170. Hence, if filter 74' is designed to pass only light that bears angles equal to 164, then such light passing outside ring 170 will be reflected, passing only light that are at angle 162 to the end face 160a after such light passes through the fiber 160.

In the preferred embodiment, however, filter 74' passes light that impinges the filter in directions normal to the surface of the filter, and light impinging at other off-normal direction angles are reflected. This is desirable because transmission of the fiber along the fiber axis is maximum, and also because such filters are more readily available. Employing the filter 74' between detector 72 and bundle 76 has the advantage that commercially available off-the-shelf type filters can be used, such as those available from CVI Laser Corporation referenced above.

The di-electric filter 74 may also be used without the optical fiber bundle 76 to collect the light scattered from spot 54, in the configuration shown in FIG. 7. As shown in FIG. 7, layer 74 will reflect the scattered light from spot 54 in all directions except those that are within the collection aperture, that is, directions substantially at azimuth angle of 45°. The light that is passed by filter 74 is then detected by photo-voltaic cells, charge coupled devices or other detectors 180.

In the above description, aperture control has been described only in reference to the horizontal plane and in terms of the azimuth angle. FIGS. 8A–8C illustrate systems for elevation collection angle control. In FIG. 8A, an aperture 200 is used to limit the light passed to the light collection system 70 in the elevation direction. In FIG. 8B, an additional filter may be used. One of the problems in the configuration of FIG. 8B is that the light reflected by the filter 74 may undergo multiple reflections to eventually appear as noise, thereby degrading signal to noise ratio. This is reduced in the configuration of FIG. 8C where a prism together with a filter are used. The front surface 202a of prism 202 facing the scan line and spot 54 is angled to direct reflections upwards away from the plane of the filter substrate 74 and fiber bundle 76. The upper surface 202b is shaped to cause total internal reflection so that substantially all of the light reaching it is transmitted to filter 74. Bottom surface 202c is shaped to reflect specular reflections away from the entire system into an optical dump. Since much of the extraneous light has been shielded by prism 202 from filter 74, the undesirable reflections described above in reference to FIG. 8B are much reduced.

As shown in FIG. 5, while filter 74 is impinged by light from many different directions originating from a single spot, only light travelling within a certain aperture will be passed. In FIG. 5, the aperture is a cone with ray 112 at its axis. Therefore, by moving filter 74, it is possible to alter the position of this aperture and therefore the direction of light that will be transmitted thereby. This is further illustrated in FIGS. 9A, 9B. AS shown in FIG. 9A, where the filter is in the position 74(1) shown, the scattered or reflected ray 252 will be normal to the surface of the filter and be reflected while ray 254 will be at 45° to the surface and will be mostly (80%) transmitted. But if the filter is rotated to the position 74(2) as shown in FIG. 9B, then ray 252 is no longer normal to the surface of the filter but bear an angle of 45° to the filter and is therefore mostly transmitted. Ray 254 will now be at a 30° to the filter and will be largely reflected. In this manner, the collection aperture of the filter may be altered. To permit a larger angle of rotation of the filter, it may be desirable to construct filter 74 so that the maximum transmission is a ray at 30° rather than at 45° to the surface of the filter. Filter 74 may be rotated about scan line 60 or a line parallel to the scan line so that the surface of the filter for receiving the scattered light remain parallel to the scan line, for reasons explained below. Filter 74 may be rotated by an airpot actuator assembly as shown in FIG. 10, which is a view showing in more detail the control mechanism of FIG. 8C to illustrate one embodiment of the invention of FIGS. 9A, 9B. By means of a solenoid (not shown) and a vacuum line 251, the actuator 253 is activated to move drive rod 255, bushing 257 and pin 259 attached to the filter, so as to rotate the filter in the elevation plane (plane of the paper) to a desired angle.

It is important to know the location of the various particles on a wafer, in order to identify them and to determine the source. This is usually done on a microscope, either optical or SEM (scanning electron microscope). Because the particles are so small and the field of view is so limited, reference must be done to a high degree of accuracy. Because of the scale of pattern features this must be done off of the actual pattern and not off of external features of the wafer. The system can scan the beam to in order to generate position information needed from the pattern signal generated by the beam. Since the collection channel is optimized to reject pattern signals, such signals often cannot be seen for alignment. Traditionally, to perform the alignment process, an additional channel is required to detect the scattered light from the pattern signals. Because all real patterned wafers contain a large number of horizontal lines, light can be collected in the plane of the incident and specular rays, resulting in a strong pattern detection system for positioning the scanning beam and scan line relative to the pattern on the wafer. With the variable collection system shown in FIGS. 9A, 9B, 10 both functions can be performed with the same channel. Where the user is interested in rejecting pattern signal for particle detection, the configuration in FIG. 9A is used to reject the normal incident light containing pattern information and collect the off axis light that will contain scattered light from particles. By rotating the filter to a position as shown in FIG. 9B, the pattern signal is now passed by the filter and alignment of the scanning beam with respect to patterns on the wafer can be performed. This is particularly useful in the case where the streets of the wafer are aligned along the scan line. While this is the preferable case, other schemes are possible.

As noted above in the Background of the Invention, in order to facilitate meaningful template comparison, it is desirable for the light collection subsystem to collect light at a constant collection angle. This is accomplished by maintaining an aperture of the light collection system substantially parallel to the scan line 60. As shown in FIGS. 2, 7, 9A and 9B, filter 74 is in a position so that its surface for receiving the scattered light is substantially parallel to the scan line 60. The end face 76a of bundle 76 in FIG. 4 is also substantially parallel to the scan line for the same reason.

FIGS. 11 and 12 are schematic views of respectively a baffle and a grating type aperture control device that can be used to replace the di-electric filter 74 in the figures described above and function in essentially the same manner as filter 74 as described above to illustrate yet other aspects of the invention. As shown in FIG. 11, Louvered baffle 260 includes a layer of filter material comprising dense black plastic vanes 262 in clear plastic 264. Absorption by the vanes is high because the black and clear plastic have substantially the same index of refraction. As shown in FIG. 11, baffle 260 can also be designed to pass light only at certain specified angles of incidence. Baffle 260 may be a sun screen material designed to block or reduce sun light to be put on substrates such as glass, such as that available from 3M Industrial Optics, 3M Center, 220-7W-06, St. Paul, Minn.

As shown in FIG. 12, grating system 270 comprises six layers of grating layers stacked together in the manner shown. Light rays 272 impinging in directions normal to the system will be reflected by stripes 274, while rays 274 at an angle of 45 degrees to the system will be passed and collected. Stripes 274 may be opaque so that they absorb instead of reflect light, which reduce undesirable stray light caused by multiple reflections to pass through grating 270.

FIG. 13 is an isometric view parallel to that of FIG. 6 illustrating an aperture control device that can be used to replace the di-electric filter 74 of FIG. 6. As shown in FIG.

13, the undesirable light rays 150', 152' and 154' can be blocked by an opaque object 300 serving as an optical stop. If desired, the hole 302 in the stop 300 can be made smaller to let through only light that passes from end 160b along or close to axis A.

FIGS. 14A, 14B, 14C are cross-sectional views of a section of an optical fiber, each with a different cladding composition or material to illustrate another aspect of the invention. If a clear or transparent cladding material 302 is used, as in FIG. 14A, such cladding may have a refractive index that is lower than that of the material 304 in the fiber, so that refraction of ray 306 takes place at the fiber/cladding interface. The ray impinges the cladding/air interface 310 at a large angle to the normal direction and may be internally reflected at such interface, thereby resulting in the ray propagating down the fiber to degrade signal-to-noise ratio.

This problem can be solved by etching away a portion of the clear cladding 302 and replacing the etched portion with a light absorbing material 320 that absorbs ray 306 as shown in FIG. 14B. It can also be solved by replacing the clear cladding by an absorptive glass cladding 340 to attenuate ray 306 as it propagates through the fiber and cladding, as illustrated in FIG. 14C.

While the invention has been described above by reference to various embodiments, it will be understood that different changes and modifications may be made without departing from the scope of the invention which is to be determined only by the appended claims.

What is claimed is:

1. An apparatus for inspecting a surface, comprising:
   a light source providing a light beam in an incident direction to a spot on said surface, said spot tracing a line on said surface as time progresses to illuminate spots along the line; and
   a collection system for collecting in directions at a substantially constant azimuth angle to the incident direction light scattered by the illuminated spots, said system rejecting scattered light not substantially at said constant azimuth angle from such spots, said azimuth angle being different from 90 degrees, and said directions for collecting light being transverse to a plane of the incident direction and a specular reflection thereof.

2. The apparatus of claim 1, wherein the collection system includes a collection aperture that spans a spatial extent of said line to collect light scattered by spots along said line.

3. The apparatus of claim 2, wherein the line covers an entire length or width of the surface, and wherein the collection aperture collects light scattered by all spots along said line.

4. The apparatus of claim 1, said collection system comprising a plurality of optical fibers with axes oriented such that scattered light from the spots travelling substantially at said azimuth angle to the incident direction is refracted substantially along the axes of the fibers.

5. The apparatus of claim 4, said collection system further comprising a filter for filtering light scattered from said spots towards the fibers or emerging from the fibers.

6. The apparatus of claim 5, said filter having a smaller collection aperture than collection angles of the fibers.

7. The apparatus of claim 5, said filter comprising a di-electric filter.

8. The apparatus of claim 7, said source supplying light of a predetermined wavelength, said filter passing light of said wavelength substantially only at said azimuth angle from the incident direction.

9. The apparatus of claim 5, said filter comprising a baffle or grating.

10. The apparatus of claim 4, said optical fibers arranged in a bundle with an end face receiving light scattered from the surface, said end face being substantially parallel to the line.

11. The apparatus of claim 1, said collection system comprising a filter.

12. The apparatus of claim 11, said filter comprising a di-electric filter.

13. The apparatus of claim 12, said source supplying light of a predetermined wavelength, said filter passing light of said wavelength substantially only at said azimuth angle to the incident direction.

14. The apparatus of claim 12, said filter having a surface that is substantially parallel to the line.

15. The apparatus of claim 12, said filter comprising a baffle or grating.

16. The apparatus of claim 1, said surface being that of a semiconductor wafer having patterned streets thereon, said incident direction being substantially parallel to the streets.

17. The apparatus of claim 1, further comprising means for limiting passage of light in the elevation direction.

18. The apparatus of claim 17, said limiting means comprising a prism or an aperture interposed between the line and the collection system.

19. A method for collection light from a surface, comprising the steps of:
   providing a light beam in an incident direction to illuminate a spot on said surface, said spot tracing a line on said surface as time progresses to illuminate spots along the line; and
   collecting in directions at a substantially constant azimuth angle to the incident direction light scattered by the illuminated spots, and rejecting scattered light not substantially at said constant azimuth angle from such spots, said azimuth angle being different from 90 degrees, and said directions for collecting light being transverse to a plane of the incident direction and a specular reflection thereof.

20. The method of claim 19, wherein the line covers an entire length or width of the surface, and wherein the collecting step collects light along directions that are spatially dispersed across said line to collect light scattered by spots along said line.

21. The method of claim 19, said surface being that of a semiconductor wafer having patterned streets thereon, said incident direction being substantially parallel to the streets.

22. The method of claim 19, said collecting step including passing said scattered light successively through two elements, wherein each of said elements has a solid angle of collection about an axis that is substantially at said azimuth angle to the incident direction.

23. The method of claim 22, said passing step passing said scattered light through a filter and a plurality of fiberoptic channels.

24. An apparatus for selectively collecting light from a surface traveling along different directions, comprising:
   a source supplying substantially monochromatic light of a predetermined wavelength to illuminate one or more spots on the surface;
   a filter having a surface, said filter including a di-electric material that passes light from said source substantially only when said light is at substantially a predetermined angle to the surface of the filter; and
   means for changing the orientation of the filter, thereby causing a first beam originally not passed by the filter to be passed by the filter, and a second beam originally passed by the filter to be not passed by the filter, said first and second beams originating from the spots.

25. The apparatus of claim 24, said predetermined angle being different than 90 degrees.

26. The apparatus of claim 25, wherein said means for changing rotates the filter.

27. The apparatus of claim 26, wherein said means for changing rotates the filter to a first position to pass specularly reflected light from the surface and to a second position to pass non-specularly scattered light.

28. The apparatus of claim 24, said source causing a light beam to trace a scan line on the surface, said changing means rotating the filter about said scan line or a line substantially parallel to the scan line.

29. A method for selectively collecting light traveling along different directions, comprising the steps of:

supplying substantially monochromatic light of a predetermined wavelength to illuminate one or more spots on the surface;

providing a filter having a surface, said filter including a di-electric material that passes light from said source substantially only when said light is at substantially a predetermined angle to the surface of the filter; and changing the orientation of the filter, thereby causing a first beam originally not passed by the filter to be passed by the filter, and a second beam originally passed by the filter to be not passed by the filter, said first and second beams originating from the one or more spots on the surface.

30. The method of claim 29, said angle being different than 90 degrees.

31. The method of claim 30, wherein said changing step rotates the filter.

32. The method of claim 31, wherein said changing step rotates the filter to a first position to pass specularly reflected light from the surface and to a second position to pass non-specularly scattered light.

33. The method of claim 29, said supplying step causing a light beam to trace a scan line on the surface, said changing step rotating the filter about said scan line or a line substantially parallel to the scan line.

34. An apparatus for detecting anomalies of the surface, comprising:

a light source providing a light beam in an incident direction to a spot on said surface, said spot tracing a line on said surface as time progresses to illuminate spots along the line; and a collection system for collecting at a substantially constant azimuth angle to the incident direction light scattered by the illuminated spots, said system rejecting scattered light not substantially at said constant azimuth angle from such spots, said azimuth angle being different from 0 and 90 degrees; and a detector receiving light from the aperture from all of said directions.

* * * * *